United States Patent
Uesugi et al.

(10) Patent No.: US 11,531,001 B2
(45) Date of Patent: Dec. 20, 2022

(54) CONTROLLED POTENTIAL ELECTROLYSIS GAS SENSOR

(71) Applicant: Riken Keiki Co., Ltd., Tokyo (JP)

(72) Inventors: Shinji Uesugi, Kasukabe (JP); Kei Ono, Kasukabe (JP); Naoyuki Miyagawa, Kasukabe (JP)

(73) Assignee: RIKEN KEIKI CO., LTD., Tokyo (JP)

( * ) Notice: Subject to any disclaimer, the term of this patent is extended or adjusted under 35 U.S.C. 154(b) by 152 days.

(21) Appl. No.: 17/042,599

(22) PCT Filed: Jan. 30, 2019

(86) PCT No.: PCT/JP2019/003083
§ 371 (c)(1),
(2) Date: Sep. 28, 2020

(87) PCT Pub. No.: WO2019/202807
PCT Pub. Date: Oct. 24, 2019

(65) Prior Publication Data
US 2021/0096097 A1    Apr. 1, 2021

(30) Foreign Application Priority Data
Apr. 20, 2018    (JP) .............................. JP2018-081117

(51) Int. Cl.
G01N 27/404    (2006.01)
G01N 33/00    (2006.01)

(52) U.S. Cl.
CPC ....... G01N 27/404 (2013.01); G01N 33/0036 (2013.01)

(58) Field of Classification Search
CPC .................................................. G01N 27/404
(Continued)

(56) References Cited

U.S. PATENT DOCUMENTS

| 5,611,908 A | 3/1997 | Matthiessen et al. |
| 6,236,873 B1 | 5/2001 | Holmstrom |

(Continued)

FOREIGN PATENT DOCUMENTS

| JP | S59-037455 A | 2/1984 |
| JP | S62-67443 A | 3/1987 |

(Continued)

OTHER PUBLICATIONS

International Search Report for the corresponding Application No. PCT/JP2019/003083 dated Apr. 16, 2019, with English translation.
(Continued)

*Primary Examiner* — Walter L Lindsay, Jr.
*Assistant Examiner* — Philipmarcus T Fadul
(74) *Attorney, Agent, or Firm* — Lucas & Mercanti, LLP

(57) ABSTRACT

The present invention has as its object the provision of a controlled potential electrolysis gas sensor capable of speedily obtaining a state in which gas concentration measurement can be conducted after the activation of a power source.
The controlled potential electrolysis gas sensor is configured to include at least a working electrode and a counter electrode which are provided in contact with an electrolytic solution and to detect a concentration of a detection target gas in a gas to be tested by detecting a current flowing between the working electrode and the counter electrode in a state in which the working electrode is controlled at a constant set potential. The controlled potential electrolysis gas sensor includes an operation control circuit that drives the controlled potential electrolysis gas sensor based on a current in a forward direction detected when the controlled potential electrolysis gas sensor is activated under energization conditions at the time of a gas detection operation.

6 Claims, 6 Drawing Sheets

(58) Field of Classification Search
USPC .......................................................... 73/31.05
See application file for complete search history.

(56) References Cited

U.S. PATENT DOCUMENTS

| | | | |
|---|---|---|---|
| 6,321,101 B1* | 11/2001 | Holmstrom | A61N 1/36557 |
| | | | 600/347 |
| 2009/0078587 A1* | 3/2009 | Farber | G01N 27/4065 |
| | | | 205/785.5 |
| 2015/0377826 A1 | 12/2015 | Sasaki et al. | |
| 2016/0258896 A1* | 9/2016 | Uesugi | G01N 27/404 |

FOREIGN PATENT DOCUMENTS

| | | |
|---|---|---|
| JP | H05-203613 A | 8/1993 |
| JP | 2010185855 A | 8/2010 |
| JP | 2011174722 A | 9/2011 |
| JP | 2012032186 A | 2/2012 |
| JP | 2016008906 A | 1/2016 |
| JP | 2016164510 A | 9/2016 |

OTHER PUBLICATIONS

EPO, Extended European Search Report for the corresponding European application No. 19789437.1, dated May 11, 2021.

* cited by examiner

CONTROLLED POTENTIAL ELECTROLYSIS GAS SENSOR

CROSS REFERENCE TO RELATED APPLICATION

This Application is a 371 of PCT/JP2019/003083 filed on Jan. 30, 2019 which, in turn, claimed the priority of Japanese Patent Application No. 2018-081117 filed on Apr. 20, 2018, both applications are incorporated herein by reference.

TECHNICAL FIELD

The present invention relates to a controlled potential electrolysis gas sensor.

BACKGROUND ART

In controlled potential electrolysis gas sensors, it generally takes some time before their concentration readings are stabilized after the start of energization.

In a controlled potential electrolysis oxygen sensor, for example, a large current flows between a working electrode and a counter electrode at an early stage after the start of energization along with the consumption of an oxygen gas remained in the interior of the sensor and the formation of an electric double layer at an interface between each electrode and an electrolytic solution. The oxygen concentration in the interior of the sensor reduces with time, and once oxygen existing around the working electrode is consumed, sensor output becomes stabilized at constant magnitude.

Also in controlled potential electrolysis gas sensors for detecting other detection target gases other than an oxygen gas, there is a difference between a potential state (equilibrium potential state) of a working electrode in a non-energized state and a measurement potential state suitable for gas concentration measurement. Thus, it takes some time before a state at an interface between the working electrode and an electrolytic solution, for example, a state of ion density at the interface, is stabilized after the activation of a power source.

As just described, the controlled potential electrolysis gas sensors, in practice, wait for their concentration readings to stabilize before gas concentration measurement is conducted. Thus, such controlled potential electrolysis gas sensors have a problem of being unable to conduct gas concentration measurement immediately after the activation of their power sources.

In view of such a problem, Patent Literature 1, for example, describes that a stabilization process of applying a voltage between a working electrode and a treatment electrode, which is provided separately from the working electrode, a counter electrode or a reference electrode, in a part that contains an electrolytic solution is performed as a technique for stabilizing output sensitivity of a controlled potential electrolysis gas sensor in a shorter amount of time.

CITATION LIST

Patent Literature

Patent Literature 1: Japanese Patent Application Laid-Open No. 2010-185855

SUMMARY OF INVENTION

Technical Problem

Even when the stabilization process described in Patent Literature 1 is performed, however, it takes several tens of minutes to perform the stabilization process of the controlled potential electrolysis gas sensor. The section of Example in Patent Literature 1 describes that it takes, for example, ten minutes to perform the stabilization process.

The present invention has been made in view of the foregoing circumstances and has as its object the provision of a controlled potential electrolysis gas sensor capable of speedily obtaining a state in which gas concentration measurement can be conducted after the activation of a power source.

Solution to Problem

A controlled potential electrolysis gas sensor according to the present invention is configured to include at least a working electrode and a counter electrode which are provided in contact with an electrolytic solution and to detect a concentration of a detection target gas in a gas to be tested by detecting a current flowing between the working electrode and the counter electrode in a state in which the working electrode is controlled at a constant set potential, wherein the controlled potential electrolysis gas sensor includes an operation control circuit that drives the controlled potential electrolysis gas sensor under energization conditions capable of obtaining a state in which a current in a reverse direction, exhibiting an inverse characteristic of a sensor output initial fluctuation characteristic based on a current in a forward direction detected when the controlled potential electrolysis gas sensor is activated under energization conditions at the time of a gas detection operation, flows between the working electrode and the counter electrode.

In the controlled potential electrolysis gas sensor of the present invention, the operation control circuit may preferably be configured to include a potentiostat that controls a potential of the working electrode so as to be the set potential, and a short circuit that short-circuits the counter electrode to an operating power source.

In the controlled potential electrolysis gas sensor having such a configuration, the short circuit may preferably be configured to include a switching element, and it may preferably be configured such that the switching element is turned on at the time of activating the sensor so as to apply a power source voltage of the operating power source to the counter electrode, and is turned off after elapse of a predetermined amount of time since the turning on of the switching element so as to stop the application of the power source voltage to the counter electrode.

Furthermore, the potentiostat may preferably include a first operational amplifier with a positive power source terminal to which the operating power source is connected and an output terminal to which the counter electrode is connected, and a second operational amplifier with an inverting input terminal to which the working electrode is connected and an output terminal which is electrically connected to the inverting input terminal so as to form negative feedback of an output, and one end of the switching element in the short circuit may preferably be electrically connected to the positive power source terminal of the first operational amplifier, and the other end of the switching element may preferably be electrically connected to the output terminal of the first operational amplifier.

Furthermore, in the controlled potential electrolysis gas sensor of the present invention, the operation control circuit may be configured to include a control unit that controls a potential of the working electrode at the time of activating the sensor to be temporarily an excessive potential higher than the set potential at the time of the gas detection operation.

Furthermore, in the controlled potential electrolysis gas sensor of the present invention, the detection target gas may preferably be an oxygen gas, and the gas to be tested may preferably be supplied to the working electrode through a pinhole.

Furthermore, the controlled potential electrolysis gas sensor of the present invention may preferably further include a reference electrode for controlling potentials of the working electrode and the counter electrode, the counter electrode and the reference electrode may preferably be disposed spaced apart from each other in the same plane, and the working electrode, the counter electrode and the reference electrode may preferably be disposed in a layered manner with an electrolytic solution retaining member interposed between the working electrode, and the counter electrode and the reference electrode.

Advantageous Effects of Invention

According to the controlled potential electrolysis gas sensor of the present invention, an amount of time required for a warming up process to stabilize sensor output at the time of activating the sensor can be significantly reduced, and a state in which concentration measurement of a detection target gas can be conducted with high reliability can be speedily obtained.

Moreover, an intended sensor output stabilization process can be reliably and easily performed regardless of the environmental condition under which the controlled potential electrolysis gas sensor is activated, or the state of the controlled potential electrolysis gas sensor, such as whether its non-energized time is long or short.

DESCRIPTION OF EMBODIMENTS

A controlled potential electrolysis gas sensor of the present invention includes at least a working electrode and a counter electrode which are provided in contact with an electrolytic solution. The controlled potential electrolysis gas sensor of the present invention includes an operation control circuit that drives the controlled potential electrolysis gas sensor under specific energization conditions.

The controlled potential electrolysis gas sensor of the present invention may be of a two-electrode type including a working electrode and a counter electrode, or of a three-electrode type including a working electrode, a counter electrode and a reference electrode. Alternatively, the controlled potential electrolysis gas sensor of the present invention may be configured to include two or more working electrodes for simultaneously detecting a plurality of respectively different detection target gases. In the controlled potential electrolysis gas sensor having such a configuration, a single counter electrode or two or more counter electrodes may be provided.

Furthermore, the controlled potential electrolysis gas sensor of the present invention may be configured in such a manner that electrodes are provided so as to be immersed in an electrolytic solution, or may be configured in such a manner that electrodes are provided in a layered manner with an electrolytic solution retaining member that retains an electrolytic solution being interposed between the electrodes.

A detection target gas in the controlled potential electrolysis gas sensor of the present invention is not limited to any particular gas as long as the gas is capable of electrolysis on the working electrode kept at a set potential.

As examples of such a detection target gas, may be mentioned an oxygen gas, a nitrogen dioxide gas, a nitrogen trifluoride gas, a chlorine gas, a fluorine gas, an iodine gas, a chlorine trifluoride gas, an ozone gas, a hydrogen peroxide gas, a hydrogen fluoride gas, a hydrogen chloride gas (a hydrochloric acid gas), an acetic acid gas, a nitric acid gas, a carbon monoxide gas, a hydrogen gas, a sulfur dioxide gas, a silane gas, a disilane gas, a phosphine gas and a germane gas.

An embodiment of the present invention will be described below in detail by taking a controlled potential electrolysis oxygen sensor as an example.

First Embodiment

Figure 1:
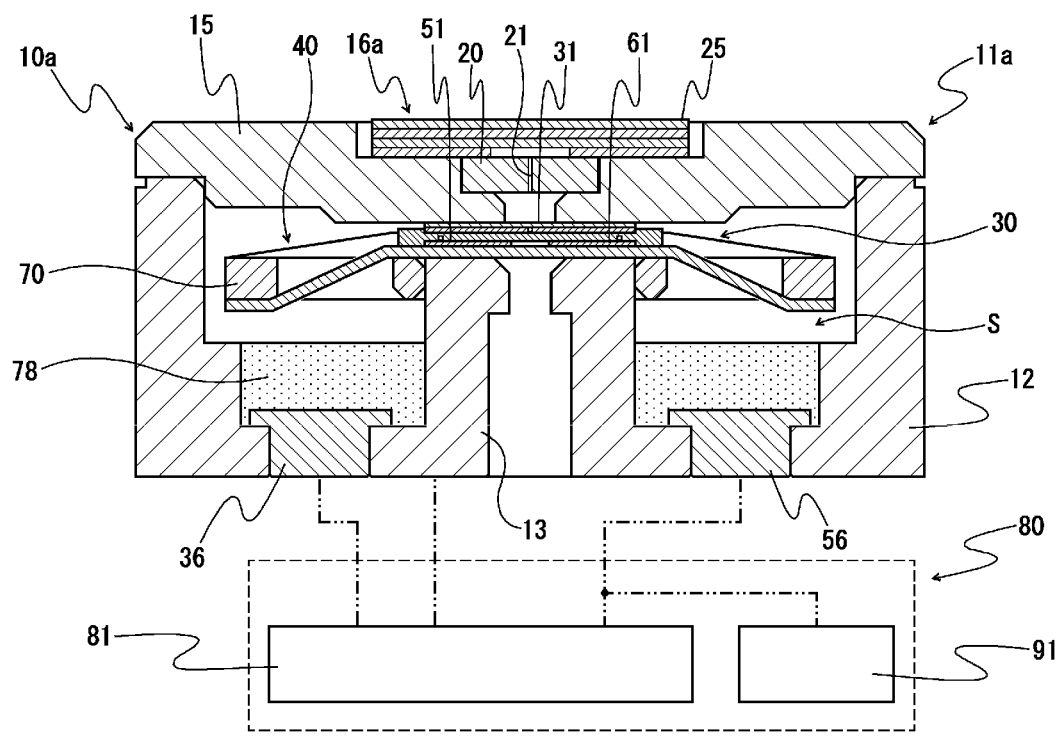
FIG. 1 is a sectional view schematically illustrating the configuration of an example of a controlled potential electrolysis oxygen sensor according to the present invention.
Figure 2:
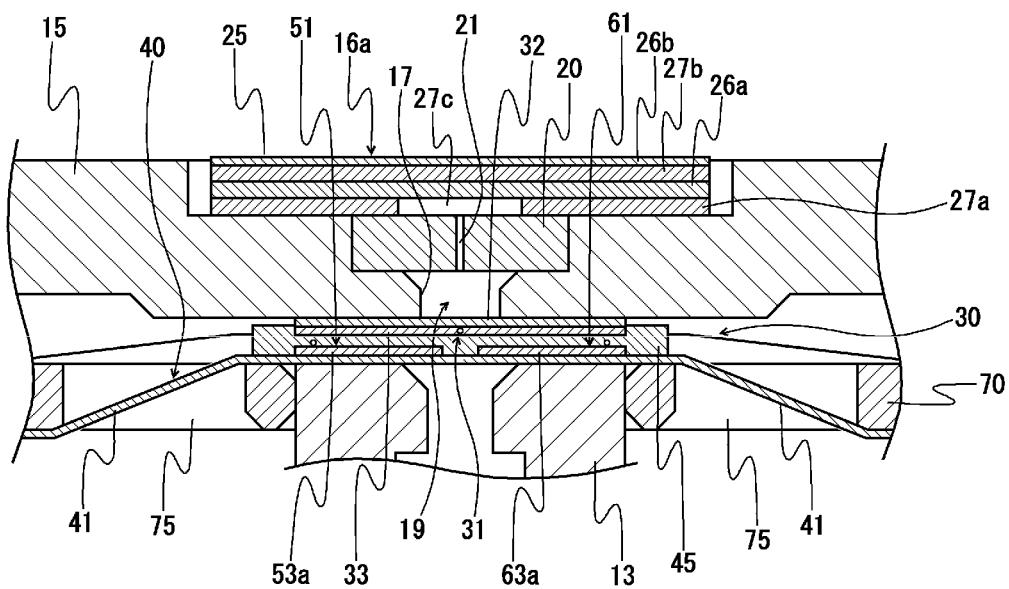
FIG. 2 is a partial sectional view illustrating, in an enlarged manner, part of the controlled potential electrolysis oxygen sensor illustrated in FIG. 1.
Figure 3:
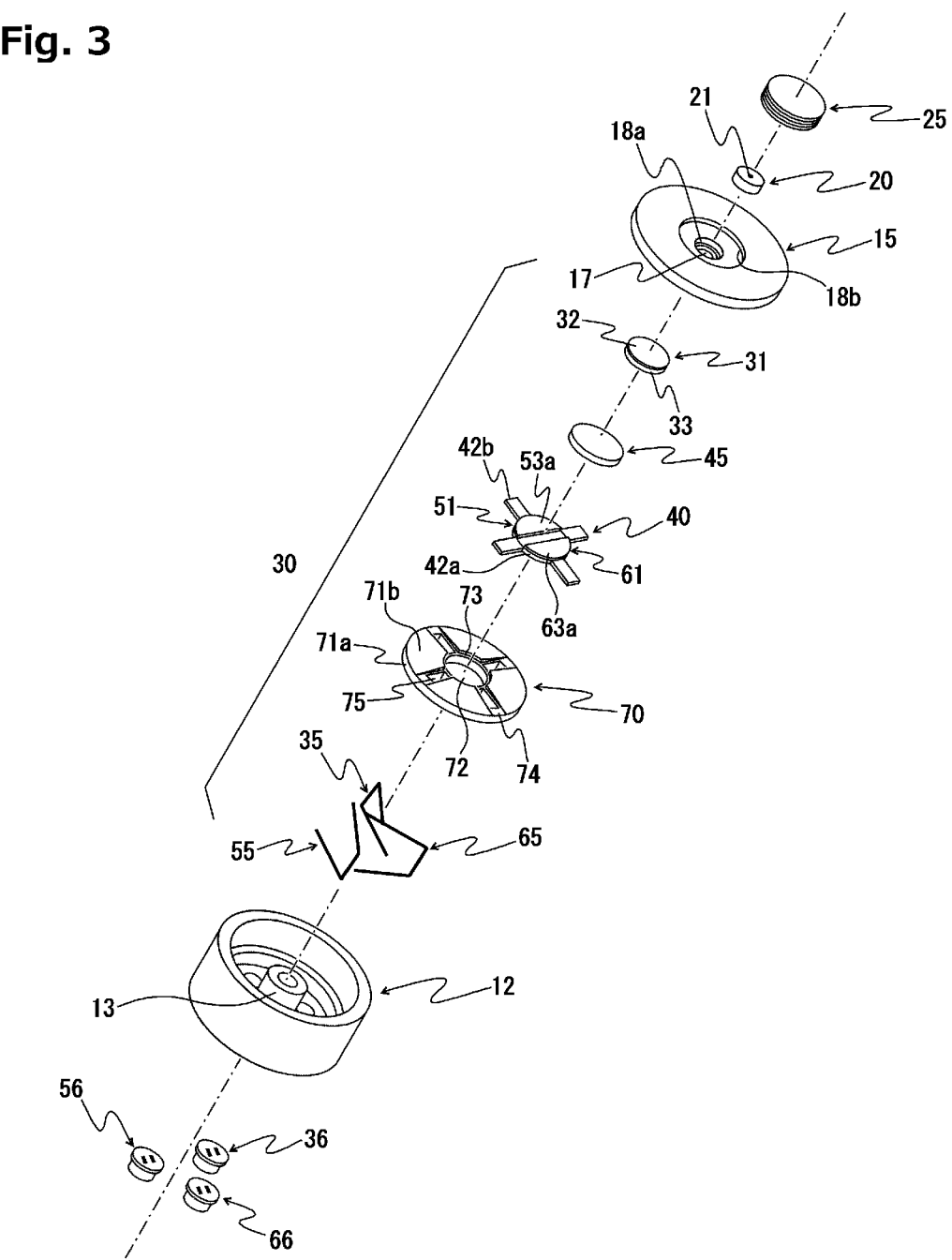
FIG. 3 is an exploded perspective view of the controlled potential electrolysis oxygen sensor illustrated in FIG. 1.

FIG. 1 is a sectional view schematically illustrating the configuration of an example of a controlled potential electrolysis oxygen sensor according to the present invention. FIG. 2 is a partial sectional view illustrating, in an enlarged manner, part of the controlled potential electrolysis oxygen sensor illustrated in FIG. 1. FIG. 3 is an exploded perspective view of the controlled potential electrolysis oxygen sensor illustrated in FIG. 1.

This controlled potential electrolysis oxygen sensor 10a includes a casing 11a that forms an electrolytic solution chamber S in which an electrolytic solution is contained.

The casing 11a is constructed by: a cylindrical casing main body 12 with one end thereof being closed; and a circular plate-shaped lid member 15 fitted into and attached to an opening of the casing main body 12.

The lid member 15 includes a gas introducing part 16a formed by a through hole 17 extending in a thickness direction thereof.

In an outer surface-side opening of the through hole 17 in the lid member 15, there are provided recesses, for example, in the shape of a two-step staircase, which form a columnar space portion having a larger diameter toward an axially outward direction.

A circular plate-shaped gas supply limiting unit 20 is disposed so as to be accommodated in a first recess 18a in the lid member 15. A buffer film 25 is disposed so as to be accommodated in a second recess 18b.

The gas supply limiting unit 20 is provided so as to be fitted into the first recess 18a with an outer peripheral edge portion of an inner surface thereof being supported by a flat surface of the first step portion.

The gas supply limiting unit 20 includes a pinhole 21 formed continuously with the through hole 17. Thus, a gas to be tested can be introduced into the casing 11a with its supply amount being limited by the pinhole 21.

The pinhole 21 has an inner diameter with a uniform dimension in an axial direction thereof. The dimension of the inner diameter of the pinhole 21 may preferably be 1.0 to 200 μm, and for example, is 50 μm. The length of the pinhole 21 is not shorter than 0.1 mm, for example.

The space portion of the through hole 17 extending in an axially inward direction from a bottom surface of the second recess 18b in the lid member 15 functions as a diffusion space for the gas to be tested, which is introduced through the pinhole 21.

The volume of the space portion functioning as a diffusion space (diffusion space portion 19) may preferably be about 0.1 to 10 $mm^3$, for example. With such a configuration, the introduced gas to be tested can be diffused sufficiently, and the amount of an oxygen gas remained in the interior of the sensor after a power source is turned off can be reduced.

The buffer film 25 in this example includes: a gas diffusion layer 26a into which the gas to be tested flows from its outer peripheral surface; and a protective layer 26b having gas impermeability and water repellency. The whole buffer film 25 is formed in a circular plate shape.

The gas diffusion layer 26a is fixed by being bonded to a bottom surface of the first recess 18a in the lid member 15 and an outer surface of the gas supply limiting unit 20 via a double-sided adhesive tape 27a.

The gas diffusion layer 26a may be constituted by a fluorocarbon resin film such as a PTFE film, for example.

The gas diffusion layer 26a may preferably have an air permeability of 0.05 to 0.5 L/day. The thickness, outer diameter dimension, porosity and other specific configurations of the gas diffusion layer 26a can be set so that its air permeability falls within the aforementioned numerical range.

The double-sided adhesive tape 27a includes a through hole 27c in communication with the internal space of the pinhole 21.

The dimension of the inner diameter of the through hole 27c may preferably be 0.05 to 5 mm, for example. The thickness of the double-sided adhesive tape 27a may preferably be 0.5 to 5 mm, for example.

With such a configuration, a sufficient level of durability against an external environment can be obtained without significantly lowering responsiveness to gas, and a stable reading can be reliably obtained.

The protective layer 26b is fixed by being bonded to an outer surface of the gas diffusion layer 26a via a double-sided adhesive tape 27b.

The protective layer 26b may be constituted by a composite film in which an aluminum foil is layered on a resin film such as PET, for example.

On a bottom wall of the casing main body 12, a cylindrical electrode holder holding part 13, which extends so as to protrude in an axially inward direction, is formed concentrically with the casing main body 12. An inner space of the electrode holder holding part 13 is opened to an external atmosphere.

On the bottom wall of the casing main body 12, a working electrode terminal 36, a counter electrode terminal 56 and a reference electrode terminal 66 are provided at positions arranged spaced apart from one another in its circumferential direction.

Inside the casing 11a, an electrode structure 30, which is constituted, for example, by three electrodes including a working electrode 31, a counter electrode 51 and a reference electrode 61 disposed in a layered manner is provided while being held by the electrode holder holding part 13.

The electrode structure 30 is configured to be held by an electrode holder 70 in a state that an electrode complex 40, which includes the counter electrode 51 and the reference electrode 61 formed in the same plane, and the working electrode 31 are layered with an electrolytic solution retaining member 45 interposed therebetween.

The electrode complex 40 is configured in such a manner that two electrode catalyst layers are arranged spaced apart from each other on one surface of a gas-permeable film 41 having a hydrophobic property. The electrode complex 40 serves also as a pressure adjusting film for adjusting internal pressure of the casing 11a.

The gas-permeable film 41 includes: a substrate part 42a having a circular plate shape; and a plurality of strip parts 42b extending in a radially outward direction from an outer peripheral edge of the substrate part 42a. In this example, four strip parts 42b are formed in a cross shape at positions arranged equally spaced apart from one another in a circumferential direction.

The two electrode catalyst layers each have a semicircular planar shape. The counter electrode 51 is constituted by one 53a of the electrode catalyst layers, and the reference electrode 61 is constituted by the other one 63a of the electrode catalyst layers.

As an example of the gas-permeable film 41, may be mentioned a porous film comprising a fluorocarbon resin such as polytetrafluoroethylene (PTFE).

Such a porous film may preferably have a Gurley number of 3 to 3000 seconds. The thickness and porosity of the porous film can be set so that its Gurley number falls within the aforementioned numerical range. For example, the porosity of the porous film may preferably be 10 to 70%, and the thickness thereof may preferably be 0.01 to 1 mm.

The one 53a of the electrode catalyst layers and the other one 63a of the electrode catalyst layers are formed through a step of firing, for example, fine particles of a catalyst metal insoluble in the electrolytic solution, fine particles of an oxide of the said catalyst metal, fine particles of an alloy of the said catalyst metal or a mixture of these fine particles together with a binder.

As examples of such a catalyst metal insoluble in the electrolytic solution, may be mentioned platinum (Pt), gold (Au), ruthenium (Ru), palladium (Pd) and iridium (Ir).

As the electrolytic solution retaining member 45, a glass fiber filter, or a non-woven fabric made of glass fibers, PP fibers, PP/PE composite fibers or ceramic fibers may be used.

The electrolytic solution retaining member 45 may preferably have an area larger than the area of an electrode forming region where the counter electrode 51 and the reference electrode 61 are formed in the electrode complex 40. The electrolytic solution retaining member 45, however, needs only to have a size allowing for its contact with the counter electrode 51 and the reference electrode 61. With the use of the electrolytic solution retaining member 45 having an area larger than the area of the electrode forming region, a sufficiently high level of electrolytic solution wettability of the electrodes can be reliably obtained.

The thickness of the electrolytic solution retaining member 45 is set to a dimension determined so as to reduce the volume of the electrolytic solution retaining member 45 as much as possible while allowing for the impregnation of the electrolytic solution retaining member 45 with a sufficient amount of the electrolytic solution. With such a configuration, gas detection can be conducted with high reliability even under a high-humidity environment. Specifically, the thickness of the electrolytic solution retaining member 45 is about 0.5 mm, for example.

The working electrode 31 has a circular plate shape having an area smaller than that of the electrolytic solution retaining member 45. The working electrode 31 is configured by forming an electrode catalyst layer 33 on one surface of a gas-permeable film 32 having a hydrophobic property.

As an example of the gas-permeable film 32 that constitutes the working electrode 31, may be mentioned a porous film comprising a fluorocarbon resin such as polytetrafluoroethylene (PTFE).

Such a porous film may preferably have a Gurley number of 3 to 3000 seconds. The thickness and porosity of the porous film can be set so that its Gurley number falls within the aforementioned numerical range. For example, the porosity of the porous film may preferably be 10 to 70%, and the thickness thereof may preferably be 0.01 to 1 mm. Such a configuration makes it easier to set a discharge characteristic to be described later so as to have an inverse characteristic of a sensor output initial fluctuation characteristic.

The electrode catalyst layer 33 that constitutes the working electrode 31 is formed through a step of firing, for example, fine particles of a catalyst metal insoluble in the electrolytic solution, fine particles of an oxide of the said catalyst metal, fine particles of an alloy of the said catalyst metal or a mixture of these fine particles together with a binder.

As examples of such a catalyst metal insoluble in the electrolytic solution, may be mentioned platinum (Pt), gold (Au), ruthenium (Ru), palladium (Pd) and iridium (Ir).

The electrode holder 70 includes: a base part 71*a* having a circular plate shape; and a tapered part 71*b* formed continuously with one surface of the base part 71*a* and having a circular truncated cone shape. The electrode holder 70 has a central through hole 72 extending in a thickness direction thereof.

A recess 73 that forms a columnar space is formed in a one surface-side opening of the central through hole 72 in the electrode holder 70, and a plurality of groove parts 74, each of which extends in a radially outward direction around the recess 73, are formed at positions arranged, for example, at equal intervals in a circumferential direction. In this example, four groove parts 74 are formed in a cross shape.

As will be described later, the electrode structure 30 is configured in such a manner that the electrolytic solution retaining member 45 is disposed on one surface side of the electrode holder 70, and the electrodes are positioned in a central part of the electrolytic solution retaining member 45. In addition, since the electrode holder 70 has the tapered part 71*b*, the electrolytic solution can be collected into the central part of the electrolytic solution retaining member 45 by a capillary phenomenon due to a minute space formed between an inclined surface of the tapered part 71*b* and a lower surface of the electrolytic solution retaining member 45 even when the electrolytic solution is reduced. Consequently, the electrodes can be stably kept in a state in contact with the electrolytic solution, and highly-reliable gas detection can be reliably conducted.

In the controlled potential electrolysis oxygen sensor 10*a*, the electrode holder 70 is disposed in such a manner that the electrode holder holding part 13 of the casing main body 12 is inserted and fitted into the central through hole 72.

The electrode complex 40 is disposed in such a manner that the substrate part 42*a* is accommodated in the recess 73 of the electrode holder 70 with the surface of the electrode complex 40 where the counter electrode 51 and the reference electrode 61 are formed facing outward, and the substrate part 42*a* occludes the central through hole 72 of the electrode holder 70. With such a configuration, the internal space of the electrolytic solution chamber S is opened to the external air via the internal space of the electrode holder holding part 13 while ensuring a liquid-tight state of the casing 11*a*. The four strip parts 42*b* of the electrode complex 40 are each accommodated so as to extend toward the electrolytic solution chamber S disposed on the lower surface side of the electrode holder 70 via a through hole 75 formed in a corresponding one of the groove parts 74 in the electrode holder 70. With such a configuration, pressure in the sensor can be kept constant through the ventilation of the interior of the sensor by the outside air regardless of the position of the controlled potential electrolysis oxygen sensor 10*a*.

The electrolytic solution retaining member 45 is disposed on one surface of the electrode complex 40.

The working electrode 31 is disposed in such a manner as to occlude an inner surface-side opening of the through hole 17 in the lid member 15 in a liquid-tight state with the electrode catalyst layer 33 being in contact with one surface of the electrolytic solution retaining member 45. Consequently, the working electrode 31, the counter electrode 51 and the reference electrode 61 become conductive via the electrolytic solution impregnated in the electrolytic solution retaining member 45.

One ends of a working electrode lead member 35, a counter electrode lead member 55 and a reference electrode lead member 65 are electrically connected to the working electrode 31, the counter electrode 51 and the reference electrode 61, respectively. The working electrode lead member 35, the counter electrode lead member 55 and the reference electrode lead member 65 are provided so as to be electrically insulated from one another in the casing 11*a*, and are electrically connected to the working electrode terminal 36, the counter electrode terminal 56 and the reference electrode terminal 66, respectively.

The working electrode lead member 35, the counter electrode lead member 55 and the reference electrode lead member 65 are each made of a metal insoluble in the electrolytic solution.

Specifically, the working electrode lead member 35, the counter electrode lead member 55 and the reference electrode lead member 65 may preferably be made of a metal selected from gold (Au), tungsten (W), niobium (Nb) and tantalum (Ta), for example.

In the controlled potential electrolysis oxygen sensor 10*a*, a sealing resin adhesive, which forms a sealing resin material layer 78 when cured, is filled into a space portion below the electrode holder 70, thereby forming a liquid-tight sealing structure.

As an example of such a sealing resin adhesive, may be mentioned an epoxy resin adhesive.

Note that the sealing resin material layer 78 is omitted for the sake of convenience in FIG. 3.

In the controlled potential electrolysis oxygen sensor 10a, each of the working electrode terminal 36, the counter electrode terminal 56 and the reference electrode terminal 66 is electrically connected to an operation control circuit 80.

The operation control circuit 80 includes a potentiostat 81 configured to control the working electrode 31 so as to have a constant set potential relative to the reference electrode 61. An exemplary configuration of the operation control circuit 80 is illustrated in FIG. 4.

The potentiostat 81 in this example is constituted by two operational amplifiers. The counter electrode 51 is electrically connected to an output terminal of a first operational amplifier 82, and the reference electrode 61 is electrically connected to an inverting input terminal (−) of the first operational amplifier 82.

The working electrode 31 is electrically connected to an inverting input terminal (−) of a second operational amplifier 85 via a resistive element 87a. An output terminal of the second operational amplifier 85 is connected to its inverting input terminal (−) via a resistive element 87b, thereby forming negative feedback of an output.

Figure 4:
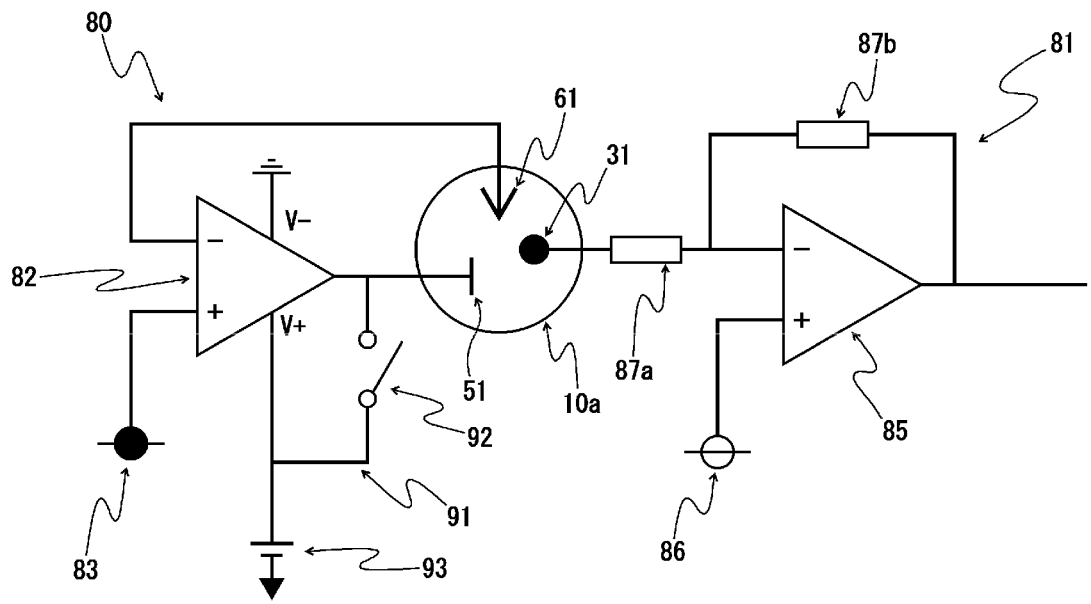
FIG. 4 is a circuit configuration diagram schematically illustrating an exemplary configuration of an operation control circuit in the controlled potential electrolysis oxygen sensor according to the present invention.

Reference numerals 83 and 86 in FIG. 4 denote reference voltage power sources connected to non-inverting input terminals (+) of the first operational amplifier 82 and the second operational amplifier 85, respectively. Reference numeral 93 denotes an operating power source connected to a positive power source terminal (V+) of the first operational amplifier 82.

The operation control circuit 80 of the above-described controlled potential electrolysis oxygen sensor 10a then has a function of driving the controlled potential electrolysis oxygen sensor 10a under energization conditions capable of obtaining a state in which a current in a reverse direction, exhibiting an inverse characteristic of a sensor output initial fluctuation characteristic based on a current in a forward direction detected when the controlled potential electrolysis oxygen sensor 10a is activated under energization conditions at the time of a gas detection operation, flows between the working electrode 31 and the counter electrode 51.

The operation control circuit 80 in this example is configured to include a short circuit 91 that short-circuits the counter electrode 51 to the operating power source 93.

The short circuit 91 includes a switching element 92 with one end thereof being electrically connected to the positive power source terminal (V+) of the first operational amplifier 82 and the other end thereof being electrically connected to the output terminal of the first operational amplifier 82.

In the controlled potential electrolysis oxygen sensor 10a, the switching element 92 is turned on at the time of activating the sensor so that a power source voltage of the operating power source 93 is applied to the counter electrode 51. After the elapse of a predetermined amount of time since the turning on of the switching element 92, the switching element 92 is turned off so as to stop the application of the power source voltage to the counter electrode 51.

When the counter electrode 51 is short-circuited to the operating power source 93 as a result of turning on the switching element 92, charge is excessively accumulated at each of an interface between the working electrode 31 and the electrolytic solution and an interface between the counter electrode 51 and the electrolytic solution as compared to when the controlled potential electrolysis oxygen sensor 10a is activated under the energization conditions at the time of the gas detection operation.

When the switching element 92 is turned off after the elapse of the predetermined amount of time since the turning on of the switching element 92, on the other hand, the accumulated charge is emitted. Consequently, there is obtained a state in which a current (reverse current) in a direction opposite to the current in the forward direction, which flows toward the working electrode 31 when the controlled potential electrolysis oxygen sensor 10a is activated under the energization conditions at the time of the gas detection operation, flows, i.e., the current flows toward the counter electrode 51.

Conditions for the application of the power source voltage to the counter electrode 51 may preferably be set so that a discharge characteristic of the accumulated charge (sensor output characteristic based on the reverse current) is identical with the inverse characteristic of the sensor output initial fluctuation characteristic at the time of activating the controlled potential electrolysis oxygen sensor 10a. The sensor output initial fluctuation characteristic represents time-dependent changes of sensor output obtained on the basis of the current in the forward direction, which flows between the working electrode 31 and the counter electrode 51 when the controlled potential electrolysis oxygen sensor 10a is activated under the energization conditions at the time of the gas detection operation. In other words, the sensor output initial fluctuation characteristic represents a transient characteristic of a current required for the consumption of oxygen remained in the interior of the sensor and the formation of a double layer at an electrode interface.

The voltage applied to the counter electrode 51, i.e., the power source voltage of the operating power source 93, may preferably be set so as to fall within a range of −5.0 to +5.0 V, for example, and an amount of time during which the power source voltage is applied to the counter electrode 51 may preferably be set to 5 to 10 seconds, for example. This makes it easier to set the discharge characteristic of the accumulated charge so as to have the inverse characteristic of the sensor output initial fluctuation characteristic.

The sensor output initial fluctuation characteristic may preferably be obtained by actually activating the controlled potential electrolysis oxygen sensor 10a. This is because an amount of time required for sensor output to stabilize after the activation of the power source is reduced if the controlled potential electrolysis oxygen sensor 10a is activated under an environmental atmosphere having a low oxygen concentration or if the controlled potential electrolysis oxygen sensor 10a having a short non-energized time is activated, and thus the conditions for the application of the power source voltage to the counter electrode 51 need to be adjusted.

Note that the sensor output initial fluctuation characteristic may be obtained by a simulation depending on the environmental condition under which the controlled potential electrolysis oxygen sensor 10a is activated, or the length of the non-energized time. If the controlled potential electrolysis oxygen sensor 10a is activated in the atmosphere (under an environment having an oxygen concentration of 20.9 vol %), for example, a sensor output initial fluctuation characteristic obtained by a simulation can be used.

An example of the case where the sensor output initial fluctuation characteristic is obtained by a simulation will be described below.

At the time of activating the sensor, the concentration of an oxygen gas remained in the interior of the sensor reduces with time, and thus a current flowing between the working electrode 31 and the counter electrode 51 also reduces with time. Thus, in the transient characteristic of the current flowing at the time of activating the sensor, the following first-order reaction formula can be assumed to be established. In the following first-order reaction formula, q represents a value given by $q=A/V \times D/\delta$, where A (cm$^2$) represents an area of the working electrode 31, V (cm$^3$) represents a volume of a porous film that constitutes the working electrode 31, D (cm$^2$/sec) represents a diffusion coefficient in the porous film, and δ (cm) represents a thickness of the porous film. In addition, t represents an elapsed time (sec) since the start of energization.

First-order reaction formula: $\log i_{(t)} = \log i_{(0)} - qt$

Figure 5:
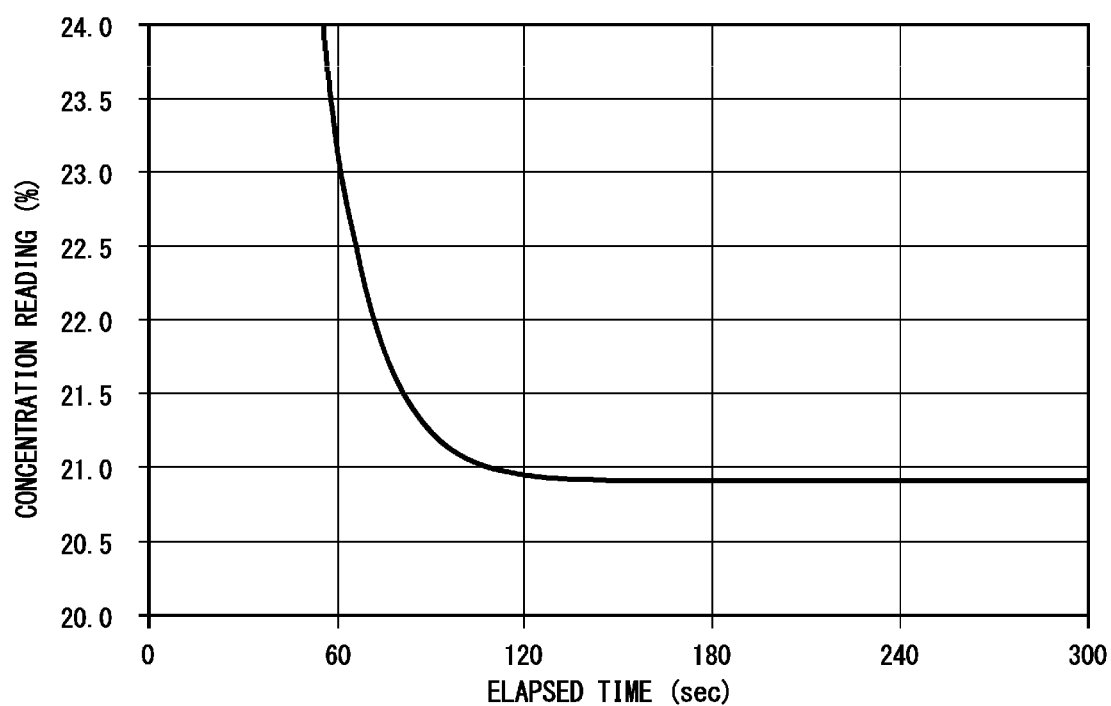
FIG. 5 is a diagram showing an example of a sensor output initial fluctuation characteristic obtained by a simulation.

Thus, the transient characteristic of the current flowing at the time of activating the sensor (the sensor output initial fluctuation characteristic) is represented by a graph as illustrated in FIG. 5, for example. This sensor output initial fluctuation characteristic approximately matches that obtained when the controlled potential electrolysis oxygen sensor 10*a* is actually activated in the atmosphere, for example.

Operations of the above-described controlled potential electrolysis oxygen sensor 10*a* will be described below.

In this controlled potential electrolysis oxygen sensor 10*a*, a gas to be tested is introduced through the pinhole 21 with the working electrode 31 being kept at a set potential having predetermined magnitude relative to the reference electrode 61. Then, by detecting an electrolytic current flowing between the working electrode 31 and the counter electrode 51 as a result of the electrolysis (reduction or oxidation) of the detection target gas in the gas to be tested in the working electrode 31, the concentration of the detection target gas in the gas to be tested is measured.

As described above, controlled potential electrolysis gas sensors generally cannot conduct gas concentration measurement immediately after the activation of their power sources. Thus, in the above-described controlled potential electrolysis oxygen sensor 10*a*, an output stabilization process for speedily stabilizing the sensor output of the controlled potential electrolysis oxygen sensor 10*a* is performed at the time of activating the sensor. The output stabilization process will be specifically described below.

Figure 6:
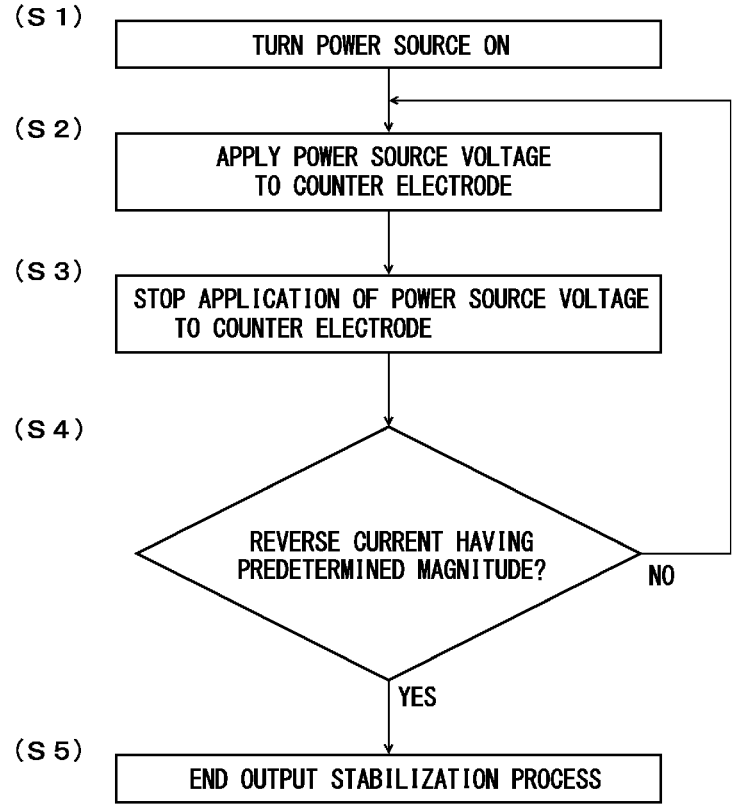
FIG. 6 is a flowchart showing an example of an output stabilization process.

In this controlled potential electrolysis oxygen sensor 10*a*, after the power source is turned on (S1) as illustrated in FIG. 6, the process of applying the voltage to the counter electrode 51 (short-circuiting process) is performed under conditions set so as to obtain a state in which the current in the reverse direction, which exhibits the inverse characteristic of the sensor output initial fluctuation characteristic specific to the controlled potential electrolysis oxygen sensor 10*a*, flows between the working electrode 31 and the counter electrode 51.

More specifically, immediately after the activation of the controlled potential electrolysis oxygen sensor 10*a*, the switching element 92 of the operation control circuit 80 is turned on so as to short-circuit the counter electrode 51 to the operating power source 93. Consequently, the power source voltage of the operating power source 93 controlled so as to have appropriate magnitude is applied to the counter electrode 51 (S2). When the power source voltage is being applied to the counter electrode 51, charge is excessively accumulated at each of the interface between the working electrode 31 and the electrolytic solution and the interface between the counter electrode 51 and the electrolytic solution as compared to the time of normal sensor activation. After the elapse of a predetermined amount of time since the start of the voltage application to the counter electrode 51, the switching element 92 of the operation control circuit 80 is turned off so as to stop the application of the power source voltage to the counter electrode 51 (S3). Consequently, the accumulated charge is emitted with an appropriately-controlled discharge characteristic.

Subsequently, a process of determining whether the output stabilization process is continued (S4) is performed in the controlled potential electrolysis oxygen sensor 10*a* on the basis of a current value obtained as of the point in time when the predetermined amount of time has elapsed since the stopping of the application of the power source voltage to the counter electrode 51 (hereinafter, referred to also as an "output value as of the determination").

In this determination process, the sensor output stabilization process is ended (S5) when a current flowing between the working electrode 31 and the counter electrode 51 is detected to be a reverse current having predetermined magnitude. When a current flowing between the working electrode 31 and the counter electrode 51 is detected not to be a reverse current having predetermined magnitude, on the other hand, the short-circuiting process is repeated (S2 and S3).

In this manner, the output stabilization process of turning on the switching element 92 of the short circuit 91 so as to apply the power source voltage of the operating power source 93 to the counter electrode 51, and turning off the switching element 92 so as to stop the voltage application to the counter electrode 51 after the elapse of the predetermined amount of time since the turning on of the switching element 92 is performed in the above-described controlled potential electrolysis oxygen sensor 10*a*. This enables the controlled potential electrolysis oxygen sensor 10*a* itself to function as a "capacitor," so to speak. That is, when the power source voltage of the operating power source 93 is being applied to the counter electrode 51, charge is excessively accumulated at each of the interface between the working electrode 31 and the electrolytic solution and the interface between the counter electrode 51 and the electrolytic solution. By stopping the application of the power source voltage to the counter electrode 51, on the other hand, the accumulated charge is emitted, thereby obtaining the state in which the current in the reverse direction, which exhibits the inverse characteristic of the sensor output initial fluctuation characteristic, flows between the working electrode 31 and the counter electrode 51. Thus, the sensor output initial fluctuation characteristic of the controlled potential electrolysis oxygen sensor 10*a* is compensated by the output characteristic (discharge characteristic) based on the reverse current.

Thus, according to the above-described controlled potential electrolysis oxygen sensor 10*a*, an amount of time required for the warming up process to stabilize sensor output at the time of activating the sensor can be significantly reduced, and a state in which concentration measurement of an oxygen gas can be conducted with high reliability can be speedily obtained.

Moreover, according to the above-described controlled potential electrolysis oxygen sensor 10*a*, the intended sensor output stabilization process can be reliably and easily performed regardless of its environmental condition (an oxygen concentration in the environmental atmosphere) under which the controlled potential electrolysis oxygen sensor 10*a* is activated, or the state of the controlled potential electrolysis oxygen sensor 10*a*, such as whether its non-energized time is long or short, by repeatedly executing the short-circuiting process until the intended condition is satisfied.

Second Embodiment

Figure 7:
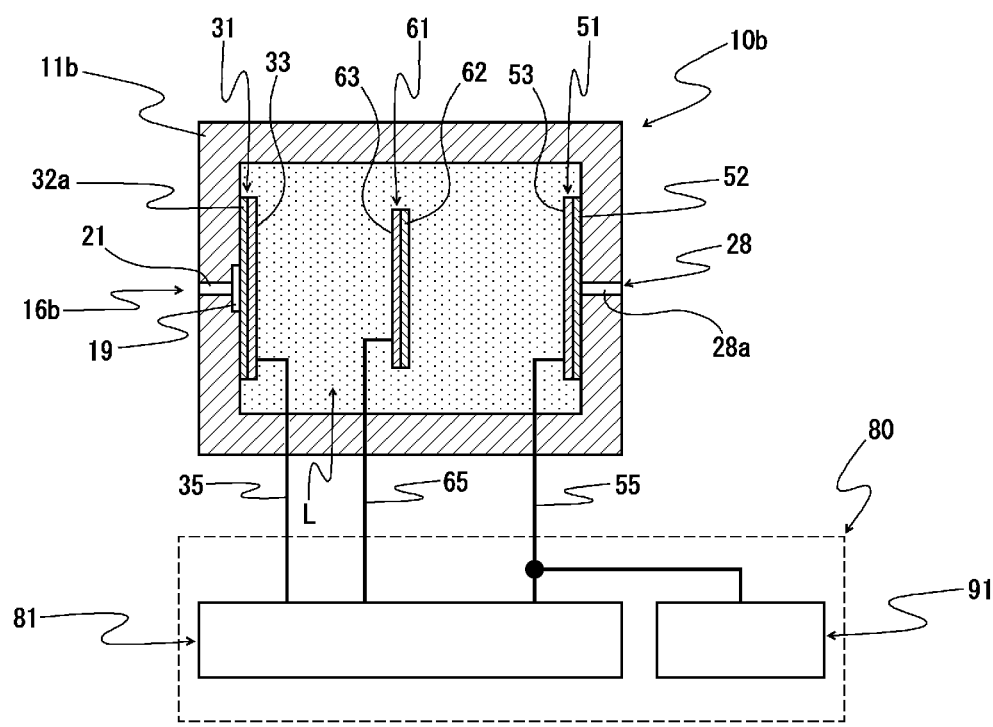
FIG. 7 is a sectional view schematically illustrating the configuration of another example of the controlled potential electrolysis oxygen sensor according to the present invention.

FIG. 7 is a diagram schematically illustrating the configuration of another example of the controlled potential electrolysis oxygen sensor according to the present invention. Note that components identical to those in FIG. 1 are denoted by the same reference numerals in FIG. 7 for the sake of convenience.

This controlled potential electrolysis oxygen sensor 10b is configured in such a manner that three electrodes including a working electrode 31, a counter electrode 51 and a reference electrode 61 are provided so as to be immersed in an electrolytic solution L.

This controlled potential electrolysis oxygen sensor 10b includes a tubular casing 11b with both ends thereof being closed. One end wall of the casing 11b includes: a recessed diffusion space portion 19 formed at a central part of its inner surface; and a gas introducing part 16b that allows for introduction of a gas to be tested, which is formed continuously with the diffusion space portion 19. The other end wall of the casing 11b includes a gas exhausting part 28.

The gas introducing part 16b is formed by a pinhole 21 having an inner diameter with a uniform dimension in an axial direction thereof, for example. Consequently, a gas to be tested is introduced into the casing 11b with its supply amount being limited by the pinhole 21. The dimension of the inner diameter of the pinhole 21 may preferably be 1.0 to 200 µm, and, for example, is 50 µm. The length of the pinhole 21 is not shorter than 0.1 mm, for example.

The volume of the diffusion space portion 19 may preferably be about 0.1 to 10 mm$^3$, for example. With such a configuration, the introduced gas to be tested can be diffused sufficiently, and the amount of an oxygen gas remained in the interior of the sensor after a power source is turned off can be reduced.

The gas exhausting part 28 is formed by a through hole 28a extending in its axial direction, for example.

A gas-permeable and hydrophobic barrier 32a on one end side is stretched tightly over an inner surface of the one end wall of the casing 11b so as to block the pinhole 21 from the inner surface side. A gas-permeable and hydrophobic barrier 52 on the other end side is stretched tightly over an inner surface of the other end wall of the casing 11b so as to block the through hole 28a, which forms the gas exhausting part 28, from the inner surface side. Consequently, an electrolytic solution chamber is formed in the casing 11b.

As an example of the gas-permeable and hydrophobic barrier 32a on one end side and the gas-permeable and hydrophobic barrier 52 on the other end side, may be mentioned one presented as an example of the gas-permeable film 32 that constitutes the working electrode 31 or the gas-permeable film 41 that constitutes the electrode complex 40 in the controlled potential electrolysis oxygen sensor 10a illustrated in FIG. 1.

The electrolytic solution chamber in the casing 11b is filled with the electrolytic solution L, and the working electrode 31, the counter electrode 51 and the reference electrode 61 are provided so as to be immersed into the electrolytic solution L.

The working electrode 31 is constituted by an electrode catalyst layer 33 provided on a wetted surface of the gas-permeable and hydrophobic barrier 32a on one end side.

The counter electrode 51 is constituted by an electrode catalyst layer 53 provided on a wetted surface of the gas-permeable and hydrophobic barrier 52 on the other end side.

The reference electrode 61 is configured in such a manner that an electrode catalyst layer 63 is formed on one surface of a gas-permeable base film 62. In this example, the reference electrode 61 is provided at a position spaced apart from each of the working electrode 31 and the counter electrode 51 in such a manner that the electrode catalyst layer 63 faces the working electrode 31.

The reference electrode 61 may alternatively be configured in such a manner that an electrode catalyst layer is formed on either side of the gas-permeable base film 62, or may alternatively be constituted solely by a catalyst metal.

As an example of the gas-permeable base film 62 that constitutes the reference electrode 61, may be used one presented as an example of the gas-permeable film 41 that constitutes the electrode complex 40 of the controlled potential electrolysis oxygen sensor 10a illustrated in FIG. 1.

One ends of a working electrode lead member 35, a counter electrode lead member 55 and a reference electrode lead member 65 are electrically connected to the working electrode 31, the counter electrode 51 and the reference electrode 61, respectively. The other ends of the working electrode lead member 35, the counter electrode lead member 55 and the reference electrode lead member 65 are drawn to the outside of the casing 11b while maintaining the liquid-tight state of the electrolytic solution chamber, and electrically connected to an operation control circuit 80.

The controlled potential electrolysis oxygen sensor 10b having such a configuration can also yield effects similar to those of the controlled potential electrolysis oxygen sensor 10a illustrated in FIG. 1. That is, according to the above-described controlled potential electrolysis oxygen sensor 10b, an amount of time required for the warming up process to stabilize sensor output at the time of activating the sensor can be significantly reduced, and a state in which concentration measurement of an oxygen gas can be conducted with high reliability can be speedily obtained. Moreover, the intended sensor output stabilization process can be reliably and easily performed regardless of differences in environmental condition (oxygen concentration in the environmental atmosphere) under which the controlled potential electrolysis oxygen sensor 10b is activated or state of the controlled potential electrolysis oxygen sensor 10b, such as whether the non-energized time is long or short.

Although the embodiments of the present invention have been described above, various changes can be made to the present invention without being limited to the above-described embodiments.

For example, in the controlled potential electrolysis gas sensor of the present invention, there is no need for the operation control circuit to include the short circuit. The operation control circuit may alternatively be configured to include a control unit configured to control the potentiostat so that the potential of the working electrode at the time of activating the sensor temporarily becomes an excessive potential higher than the set potential at the time of the gas detection operation. Even when such an output stabilization process is performed, a state in which a current in the reverse direction, which exhibits the inverse characteristic of the sensor output initial fluctuation characteristic, flows between the working electrode and the counter electrode can be obtained.

Furthermore, also by lowering the power source voltage of the reference voltage power source 86 connected to the second operational amplifier 85 in the potentiostat 81 illustrated in FIG. 4, a state in which a current in the reverse direction, which exhibits the inverse characteristic of the sensor output initial fluctuation characteristic, flows between the working electrode and the counter electrode can be obtained.

Furthermore, in the controlled potential electrolysis gas sensor of the present invention, there is no need for an environmental atmosphere at the time of activating the sensor to include a detection target gas. The controlled potential electrolysis gas sensor of the present invention may be activated in an environmental atmosphere including no detection target gas.

Furthermore, in the controlled potential electrolysis oxygen sensor illustrated in FIG. 1, there is no need for the counter electrode and the reference electrode to be formed in the same plane. The controlled potential electrolysis oxygen sensor may alternatively be configured in such a manner that the working electrode, the counter electrode and the reference electrode are layered with an electrolytic solution retaining member interposed between the respective electrodes. The same applies also to controlled potential electrolysis gas sensors for detecting other detection target gases other than an oxygen gas.

Furthermore, the controlled potential electrolysis oxygen sensor illustrated in FIG. 6 may alternatively be configured in such a manner that the reference electrode is provided on the wetted inner surface of the gas-permeable and hydrophobic barrier on the other end side at a position spaced apart from, and arranged next to, the counter electrode. The same applies also to controlled potential electrolysis gas sensors for detecting other detection target gases other than an oxygen gas.

EXAMPLE

A specific example of the present invention will be described below.

Example 1

Figure 8:
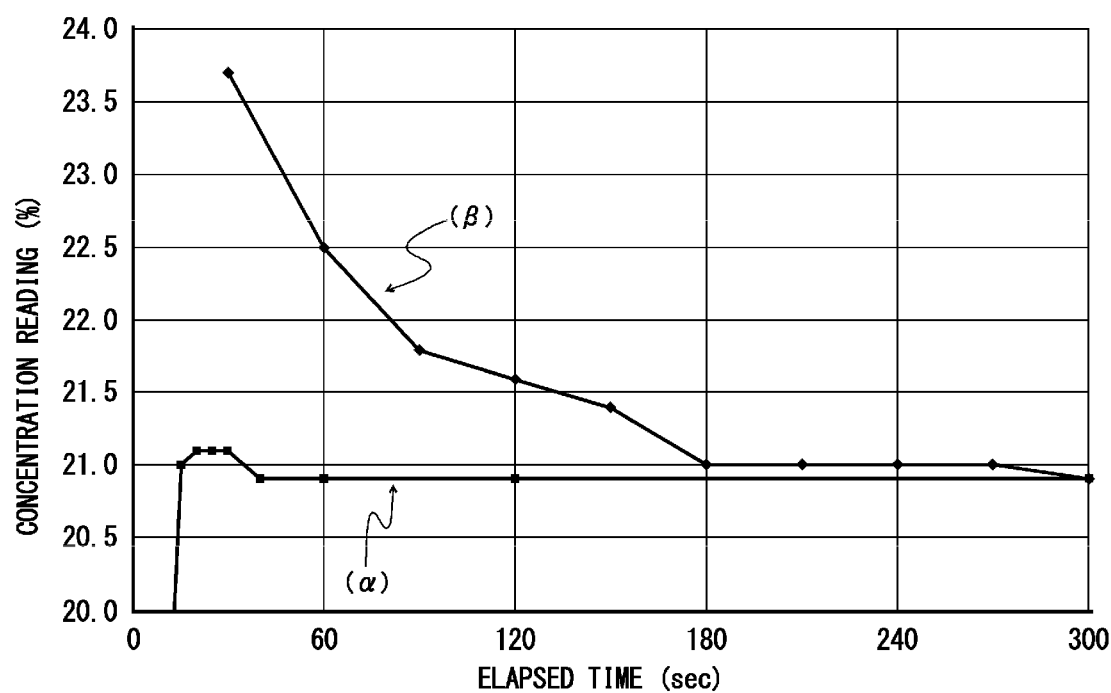
FIG. 8 is a graph showing time-dependent changes of concentration readings obtained in Example 1 and Comparative Example 1.

A controlled potential electrolysis oxygen sensor according to the present invention was produced so as to have the configuration illustrated in FIGS. 1 to 3, and the controlled potential electrolysis oxygen sensor was activated in the atmosphere (an oxygen concentration of 20.9 vol %) under energization conditions shown below. Time-dependent changes in its concentration reading are indicated by a curve (α) in FIG. 8.

Energization Conditions:
A set potential of a working electrode (31) relative to a reference electrode (61): −0.6 V
A power source voltage of an operating power source (93) to be applied to a counter electrode (51) at the time of activating the sensor: 3.0 V
An amount of time during which the power source voltage is applied to the counter electrode (51) at the time of activating the sensor: 1.0 sec Consequently, it was confirmed that a stable state of the concentration reading was able to be obtained as of the point in time when about 20 seconds were elapsed after the activation of the controlled potential electrolysis oxygen sensor.

Comparative Example 1

The controlled potential electrolysis oxygen sensor was activated in the same manner as that in Example 1 except that no power source voltage was applied to the counter electrode at the time of activating the sensor. Time-dependent changes in its concentration reading are indicated by a curve (β) in FIG. 8.

As the result, it was confirmed that about 300 seconds were required until the concentration reading was stabilized after the activation of the controlled potential electrolysis oxygen sensor.

On the basis of these results, it was confirmed that an amount of time required for the warming up process to stabilize sensor output can be significantly reduced, and a state in which concentration measurement of an oxygen gas can be conducted with high reliability can be speedily obtained by performing the output stabilization process of the present invention at the time of activating the sensor.

Moreover, an amount of time taken until the concentration reading was stabilized after the activation of the controlled potential electrolysis oxygen sensor was checked under the same conditions as those in Example 1 except that the environmental atmosphere under which the controlled potential electrolysis oxygen sensor was activated was an atmosphere having a low oxygen concentration. As the result, it was confirmed that a state in which concentration measurement of an oxygen gas can be conducted with high reliability can be speedily obtained as compared to the time of normal sensor activation.

Furthermore, an amount of time taken until the concentration reading was stabilized after the activation of the controlled potential electrolysis oxygen sensor was checked under the same conditions as those in Example 1 except that the length of its non-energized time of the controlled potential electrolysis oxygen sensor was appropriately changed. As the result, it was confirmed that a state in which concentration measurement of an oxygen gas can be conducted with high reliability can be speedily obtained as compared to the time of normal sensor activation.

REFERENCE SIGNS LIST 10a controlled potential electrolysis oxygen sensor
10b controlled potential electrolysis oxygen sensor
11a casing
11b casing
12 casing main body
13 electrode holder holding part
15 lid member
16a gas introducing part
16b gas introducing part
17 through hole
18a first recess
18b second recess
19 diffusion space portion
20 gas supply limiting unit
21 pinhole
25 buffer film
26a gas diffusion layer
26b protective layer
27a double-sided adhesive tape
27b double-sided adhesive tape
27c through hole
28 gas exhausting part
28a through hole
30 electrode structure
31 working electrode
32 gas-permeable film
32a gas-permeable and hydrophobic barrier on one end side
33 electrode catalyst layer
35 working electrode lead member
36 working electrode terminal
40 electrode complex
41 gas-permeable film
42a substrate part
42b strip part
45 electrolytic solution retaining member
51 counter electrode 52 gas-permeable and hydrophobic barrier on the other end side
53 electrode catalyst layer
53a one of electrode catalyst layers
55 counter electrode lead member
56 counter electrode terminal
61 reference electrode
62 gas-permeable base film
63 electrode catalyst layer
63a the other one of electrode catalyst layers
65 reference electrode lead member
66 reference electrode terminal
70 electrode holder
71a base part
71b tapered part
72 central through hole
73 recess
74 groove part
75 through hole
78 sealing resin material layer
80 operation control circuit
81 potentiostat
82 first operational amplifier
83 reference voltage power source
85 second operational amplifier
86 reference voltage power source
87a resistive element
87b resistive element
91 short circuit
92 switching element
93 operating power source
L electrolytic solution
S electrolytic solution chamber

The invention claimed is:

1. A controlled potential electrolysis gas sensor including at least a working electrode and a counter electrode which are provided in contact with an electrolytic solution to detect a concentration of a detection target gas in a gas to be tested by detecting a current flowing between the working electrode and the counter electrode in a state in which the working electrode is controlled at a constant set potential, the controlled potential electrolysis gas sensor comprising an operation control circuit configured to drive the controlled potential electrolysis gas sensor for a predetermined amount of time from an activation of an operating power source, under energization conditions capable of obtaining a state in which a current in a reverse direction, exhibiting an output characteristic compensating a sensor output initial fluctuation characteristic based on a current in a forward direction detected when the controlled potential electrolysis gas sensor is activated under energization conditions at a time of a gas detection operation, flows between the working electrode and the counter electrode, wherein the operation control circuit includes a potentiostat configured to control the working electrode so as to have the constant set potential, the potentiostat includes an operational amplifier having an output terminal connected to the counter electrode, the operational amplifier includes a non-inverting input terminal and a positive power source terminal, the non-inverting input terminal is connected to a reference voltage power source, and the positive power source terminal is connected to the operating power source, the operation control circuit further includes a short circuit that short-circuits the counter electrode to the operating power source, the operation control circuit is configured to apply a power source voltage of the operating power source to the counter electrode by the short circuit to obtain a state in which the current in the reverse direction flows between the working electrode and the counter electrode.

2. The controlled potential electrolysis gas sensor according to claim 1, wherein:
the short circuit includes a switching element, and
the switching element is turned on at the time of activating the sensor so as to apply the power source voltage of the operating power source to the counter electrode, and is turned off after elapse of a predetermined amount of time since the turning on of the switching element so as to stop the application of the power source voltage to the counter electrode.

3. The controlled potential electrolysis gas sensor according to claim 2, wherein:
the operational amplifier includes a first operational amplifier with the positive power source terminal to which the operating power source is connected and the output terminal to which the counter electrode is connected, and a second operational amplifier with an inverting input terminal to which the working electrode is connected and an output terminal which is electrically connected to the inverting input terminal so as to form negative feedback of an output, each of the first and second operational amplifier includes the non-inverting input terminal, and
one end of the switching element in the short circuit is electrically connected to the positive power source terminal of the first operational amplifier, and the other end of the switching element is electrically connected to the output terminal of the first operational amplifier.

4. The controlled potential electrolysis gas sensor according to claim 1, wherein the operation control circuit includes a control unit that controls a potential of the working electrode at the time of activating the sensor to be temporarily an excessive potential higher than the set potential at the time of the gas detection operation.

5. The controlled potential electrolysis gas sensor according to claim 1, wherein the detection target gas is an oxygen gas, and the gas to be tested is supplied to the working electrode through a pinhole.

6. The controlled potential electrolysis gas sensor according to claim 1, further comprising a reference electrode for controlling potentials of the working electrode and the counter electrode, wherein
the counter electrode and the reference electrode are disposed spaced apart from each other in a same plane, and
the working electrode, the counter electrode and the reference electrode are disposed in a layered manner with an electrolytic solution retaining member interposed between the working electrode, and the counter electrode and the reference electrode.

* * * * *